United States Patent
Turos et al.

(10) Patent No.: US 9,433,581 B2
(45) Date of Patent: Sep. 6, 2016

(54) POLY(VINYL BENZOATE) NANOPARTICLES FOR MOLECULAR DELIVERY

(71) Applicants: Edward Turos, Wesley Chapel, FL (US); Raphael Labruere, Creteil (FR); Ryan Scott Cormier, Tampa, FL (US); Renaud Sicard, Coral Gables, FL (US)

(72) Inventors: Edward Turos, Wesley Chapel, FL (US); Raphael Labruere, Creteil (FR); Ryan Scott Cormier, Tampa, FL (US); Renaud Sicard, Coral Gables, FL (US)

(73) Assignee: University of South Florida, Tampa, FL (US)

( * ) Notice: Subject to any disclaimer, the term of this patent is extended or adjusted under 35 U.S.C. 154(b) by 167 days.

(21) Appl. No.: 13/897,868

(22) Filed: May 20, 2013

(65) Prior Publication Data

US 2013/0243832 A1    Sep. 19, 2013

Related U.S. Application Data

(63) Continuation of application No. PCT/US2011/061429, filed on Nov. 18, 2011.

(60) Provisional application No. 61/415,003, filed on Nov. 18, 2010.

(51) Int. Cl.
| | |
|---|---|
| A61K 9/14 | (2006.01) |
| A61K 9/00 | (2006.01) |
| A61K 9/10 | (2006.01) |
| A61K 9/51 | (2006.01) |
| A61K 47/10 | (2006.01) |
| A61K 47/48 | (2006.01) |
| A61K 49/00 | (2006.01) |

(52) U.S. Cl.
CPC .......... *A61K 9/146* (2013.01); *A61K 9/0019* (2013.01); *A61K 9/10* (2013.01); *A61K 9/5138* (2013.01); *A61K 47/10* (2013.01); *A61K 47/489* (2013.01); *A61K 49/0039* (2013.01); *A61K 49/0043* (2013.01); *A61K 49/0093* (2013.01)

(58) Field of Classification Search
None
See application file for complete search history.

(56) References Cited

U.S. PATENT DOCUMENTS

| | | |
|---|---|---|
| 7,988,949 B2 | 8/2011 | Sung et al. |
| 2005/0266090 A1 | 12/2005 | Prokop et al. |
| 2008/0182776 A1 | 7/2008 | Lee et al. |
| 2009/0123507 A1* | 5/2009 | Ohrlein et al. ........ 424/421 |
| 2009/0169635 A1 | 7/2009 | Schwarz et al. |
| 2009/0297613 A1 | 12/2009 | Ringe et al. |
| 2010/0278920 A1 | 11/2010 | Turos et al. |
| 2010/0331373 A1 | 12/2010 | Egashira |
| 2011/0135744 A1 | 6/2011 | Chin et al. |
| 2011/0218140 A1 | 9/2011 | Gonsalves et al. |

OTHER PUBLICATIONS

A. Besheer et al., Tracking the urinary excretion of high molar mass poly(vinyl alcohol): J. Biomed. Mater. Res. 2007. vol. 82B:383-389.
A. Kumari et al., Biodegradable polymeric nanoparticles based drug delivery systems, Colloids Surf. B: Biointerfaces. 2010. vol. 75:1-18.
C. Lherm et al., Alkylcyanoacrylate drug carriers: II. Cytotoxicity of cyanoacrylate nanoparticles with different alkyl chain length, Int. J. Pharm. 1992. vol. 84:13-22.
C. Lombry et al., Confocal imaging of rat lungs following intratracheal delivery of dry powders or solutions of fluorescent probes. J. Control. Release. 2002. vol. 83:331-341.
D.A. Norris et al, Determining the absolute surface hydrophobicity of microparticulates using thin layer wicking, J. Control. Release. 1999. vol. 59:173-185.
D.E. Owens III and N.A. Peppas, Opsonization, biodistribution, and pharmacokinetics of polymeric nanoparticles. Int. J. Pharm. 2006. vol. 307:93-102.
E. Jeon et al., Pluronic-grafted poly-(L)-lysine as a new synthetic gene carrier. J. Biomed. Mater. Res. 2003. vol. 66A:854-859.
E. Turos et al., Penicillin-bound polyacrylate nanoparticles: restoring the activity of beta-lactam antibiotics against MRSA. Bioorg. Med. Chem. Lett. 2007. vol. 17:3468-3472.
E. Turos et al., Antibiotic-conjugated polyacrylate nanoparticles: new opportunities for development of anti-MRSA agents. Bioorg. Med. Chem. Lett. 2007. vol. 17:53-56.
H. Fessi et al., Nanocapsule formation by interfacial polymer deposition following solvent displacement, Int. J. Pharm. 1989. vol. 55:R1-4.

(Continued)

*Primary Examiner* — Hasan Ahmed
(74) *Attorney, Agent, or Firm* — Michele L. Lawson; Smith & Hopen, P.A.

(57) ABSTRACT

The present invention comprises poly(vinyl benzoate) nanoparticle suspensions as molecular carriers. These nanoparticles can be formed by nanoprecipitation of poly(vinyl benzoate) in water using Pluronic F68 as surfactant, to create spherical nanostructures measuring about 200-250 nm in diameter which are stable in phosphate buffer and blood serum, and only slowly degrade in the presence of esterases. Kinetics experiments in phosphate buffer indicate that 78% of the coumarin-6 was encapsulated within the polymer matrix of the nanoparticle, and the residual 22% of coumarin-6 was surface-bound and quickly released. The nanoparticles are non-toxic in vitro towards human epithelial cells ($IC_{50}$>1000 μg/mL) and primary bovine primary aortic endothelial cells ($IC_{50}$>500 μg/mL), and exert non-observable bactericidal activity against a selection of representative test microbes (MIC>250 μg/mL). Poly(vinyl benzoate) nanoparticles are suitable carriers for molecular delivery of lipophilic small molecules such as drugs pharmaceutical and imaging agents.

13 Claims, 6 Drawing Sheets

(56) References Cited

OTHER PUBLICATIONS

J. Garay-Jimenez et al., Methods for purifying and detoxifying sodium dodecyl sulfate-stabilized polyacrylate nanoparticles. Nanomed: Nanotech. Biol. Med. 2008. vol. 4:98-105.

J. Garay-Jimenez et al., Physical properties and biological activity of poly(butyl acrylate-styrene) nanoparticle emulsions prepared with conventional and polymerizable surfactants. Nanomed: Nanotech. Biol. Med. 2009. vol. 5:443-451.

J. Panyam and V. Labhasetvvar, Biodegradable nanoparticles for drug and gene delivery to cells and tissue. Adv. Drug Deily. Rev. 2012. vol. 64:61-71.

J.M. Anderson and M.S. Shive, Biodegradation and biocompatibility of PLA and PLGA microspheres. Adv. Drug . Deily. Rev. 1997. vol. 28:5-24.

J.M. Chan et al., PLGA-lecithin-PEG core-shell nanoparticles for controlled drug delivery. Biomaterials. 2009. vol. 30:1627-1634.

J.S. Chawla and M.M. Amiji. Biodegradable poly(epsilon-caprolactone) nanoparticles for tumor-targeted delivery of tamoxifen, Int. J. Pharm. 2002. vol. 249:127-138.

J.W. Longworth, Conformations and interactions of excited states. I. Model compounds for polymers. Biopolymers. 1966. vol. 4:1115-1129.

K. Greenhalgh and E. Turos, In vivo studies of polyacrylate nanoparticle emulsions for topical and systemic applications. Nanomed: Nanotech. Biol. Med. 2009. vol. 5:46-54.

K. Lahnstein et al., Pulmonary absorption of aerosolized fluorescent markers in the isolated rabbit lung, Int. J. Pharm. 2008. vol. 351:158-164.

K. Lee and J. Hong, Nonionic adsorption of aromatic amino acids on a cation-exchange resin. React. Funct. Polym. 1995. vol. 28.75-80.

K.S. Soppimath et al., Biodegradable polymeric nanoparticles as drug delivery devices, J. Control. Release. 2001. vol. 70:1-20.

K.Y. Win and S.-S. Feng, Effects of particle size and surface coating on the cellular uptake of polymeric nanoparticles for oral delivery of anticancer drugs. Biomaterials. 2005. vol. 26:2713-2722.

L. Krähenbühl et al., Benzoic acid metabolism reflects hepatic mitochondrial function in rats with long-term extrahepatic cholestasis. Hepatology. 1997. vol. 25 (No. 2):278-283.

M. Brzoska et al., Incorporation of biodegradable nanoparticles into human airway epithelium cells—in vitro study of the suitability as a vehicle for drug or gene delivery in pulmonary diseases. Biochem. Biophys. Res. Commun. 2004. vol. 318:562-570.

M.C. Venier-Julienne and J.P. Benoît, Preparation, purification and morphology of polymeric nanoparticles as drug carriers. Pharm. Acta Helv. 1996. vol. 71:121-128.

M.L.T. Zweers et al., In vitro degradation of nanoparticles prepared from polymers based on DL-lactide, glycolide and poly(ethylene oxide). J. Control. Release 2004. vol. 100:347-356.

M.P. Desai et al., The mechanism of uptake of biodegradable microparticles in Caco-2 cells is size dependent. Pharm. Res. 1997. vol. 14 (No. 11):1568-1573.

National Committee for Clinical Laboratory Standards, Methods for dilution antimicrobial susceptibility tests for bacteria that grow aerobically-seventh edition (2006): Approved Standard M7-A7, vol. 26 (No. 2), 15, NCCLS,Wayne, PA, USA.

P. Beck et al., Influence of polybutylcyanoacrylate nanoparticles and liposomes on the efficacy and toxicity of the anticancer drug mitoxantrone in murine tumour models, J. Microencapsul. 1993. vol. 10 (No. 1):101-114.

R.H. R H Müller et al., Nanosuspensions as particulate drug formulations in therapy Rationale for development and what we can expect for the future, Adv. Drug Deily. Rev. 2001. vol. 47:3-19.

R.H. Müller et al., In vitro model for the degradation of alkylcyanoacrylate nanoparticles, Biomaterials. 1990. vol. 11 (Issue 8):590-595.

R.H. Müller et al., Cytotoxicity of magnetite-loaded polylactide, polylactide/glycolide particles and solid lipid nanoparticles. Int. J. Pharm. 1996. vol. 138:85-94.

S.C. Abeylath et al., Glyconanobiotics: novel carbohydrated nanoparticle antibiotics for MRSA and Bacillus anthracis, Bioorg. Med. Chem. 2008. vol. 16:2412-2418.

S.C. Abeylath and E. Turos, Glycosylated polyacrylate nanoparticles by emulsion polymerization, Carb. Polym. 2007. vol. 70:32-37.

T. Hirose et al., Gas transport in poly(vinyl benzoate). J. Appl. Poly. Sci. 1985. vol. 30:401-410.

T. Yamaoka et al., Comparison of body distribution of poly(vinyl alcohol) with other water-soluble polymers after intravenous administration. J. Pharm. Pharmacol. 1995. vol. 47:479-486.

V. Lenaerts et al., Degradation of poly(isobutyl cyanoacrylate) nanoparticles, Biomaterials. 1984. vol. 5 (Issue2):65-68.

Y. Dong, and S.-S. Feng, Poly(D, L-lactide-co-glycolide) (PLGA) nanoparticles prepared by high pressure homogenization for paclitaxel chemotherapy. Int. J. Pharm. 2007. vol. 342:208-214.

Z. Gan et al., Enzymatic degradation of poly($\epsilon$-caprolactone)/poly(DL-lactide) blends in phosphate buffer solution. Polymer 1999. vol. 40:2859-2862.

Muthu and Singh, Poly (D, L-Lactide) Nanosuspensions of Risperidone for Parenteral Delivery: Formulation and In-Vitro Evaluation. Current Drug delivery. 2009. vol. 6 (No. 1):62-68.

C. Pinto Reis et al., Nanoencapsulation I. Methods for preparation of drug-loaded polymeric nanoparticles. Nanomedicine: Nanotechnology, Bio., and Med. 2006. vol. 2:8-21.

Labruere et al., Poly(vinyl benzoate) nanoparticles for molecular delivery: Studies on their preparation and in vitro properties. Journal of Controlled Release. 2010. vol. 148:234-240.

International Search Report for PCT/US2011/061429 (filing date Nov. 18, 2011) with a mailing date of Jun. 29, 2012, Applicant: University of South Florida et al.

Preliminary Report of Patentability for PCT/US2011/061429 (filing date Nov. 18, 2011) with a issuance date of May 21, 2013, Applicant: University of South Florida et al.

G. Agusti, et al., Radiopaque iodinated ethers of poly(vinyl iodobenzyl ether)s: Synthesis and evaluation for endovascular embolization. Journal of Applied Polymer Science, 2015, 132, 41791, 1-13.

\* cited by examiner

Coumarin 6

5(6)-Carboxyfluorescein

POLY(VINYL BENZOATE) NANOPARTICLES FOR MOLECULAR DELIVERY

CROSS REFERENCE TO RELATED APPLICATIONS

This application is a continuation of prior filed International Application, Serial Number PCT/US2011/061429 filed Nov. 18, 2011, which claims priority to U.S. Provisional Application No. 61/415,003 entitled "Poly(Vinyl Benzoate) Nanoparticles For Molecular Delivery", filed Nov. 18, 2010, the contents of which are hereby incorporated by reference into this disclosure.

STATEMENT OF GOVERNMENT INTEREST

This invention was made with government support under Grant No. 0620572, awarded by the National Science Foundation. The Government has certain rights in the invention.

FIELD OF INVENTION

The present invention relates to a novel nanoparticle delivery carrier for small molecules such as pharmaceutical and imaging agents.

BACKGROUND OF THE INVENTION

Biodegradable polymeric nanoparticles have been intensively studied as a possible way to reduce drug toxicity and degradation, while enhancing the residence time and drug concentration at the desired site of action (K. S. Soppimath, T. M. Aminabhavi, A. R. Kulkarni, W. E. Rudzinski, Biodegradable polymeric nanoparticles as drug delivery devices, J. Control. Release 70 (1-2) (2001) 1-20; J. Panyam, V. Labhaserwar, Biodegradable nanoparticles for drug and gene delivery to cells and tissue, Adv. Drug Deliv. Rev. 55 (3) (2003) 329-347; A. Kumari, S. K. Yadav, S. C. Yadav, Biodegradable polymeric nanoparticles based drug delivery systems, Colloids Surf. B: Biointerfaces 75 (1) (2010) 1-18). Biodegradability is an important attribute of a nanoparticle carrier for several reasons, including the ability to control-release the bound molecule in a sustained, programmable way, and to provide the means for the final removal of the carrier from the body in an innocuous form. Several biodegradable polymers have been used for this application: polylactides (PLA), co-polymers of lactic/glycolic acids (PLGA) and poly(alkylcyanoacrylates) (PACA) are among the most widely investigated for drug delivery. For these systems, two degradation pathways have been identified: the erosion of poly(hydroxy acids) due to a main chain scission mechanism and the PACA biodegradation by side chain cleavage (V. Lenaerts, P. Couvreur, D. Christiaens-Leyh, E. Joiris, M. Roland, B. Rollman, P. Speiser, Degradation of poly(isobutyl cyanoacrylate) nanoparticles, Biomaterials 5 (2) (1984) 65-68: R. H. Müller, C. Lherm, J. Herbort, P. Couvreur, In vitro model for the degradation of alkylcyanoacrylate nanoparticles, Biomaterials 11 (8) (1990) 590-595; J. M. Anderson, M. S. Shive, Biodegradation and biocompatibility of PLA and PLGA microspheres, Adv. Drug Deliv. Rev. 28 (1) (1997) 5-24; M. L. T. Zweers, G. H. M. Engbers, D. W. Grijpma, J. Feijen, In vitro degradation of nanoparticles prepared from polymers based on DL-lactide, glycolide and poly(ethylene oxide), J. Control. Release 100 (3) (2004) 347-356).

Release of entrapped molecules from within the matrix occurs mainly with polymer degradation, as has been reported for poly(hydroxy acid) nanoparticles (J. M. Anderson, M. S. Shive, Biodegradation and biocompatibility of PLA and PLGA microspheres, Adv. Drug Deliv. Rev. 28 (1) (1997) 5-24). Moreover, it has been shown that PLA and PLGA nanoparticles significantly affect the viability of human granulocytes (R. H. Mailer, S. Maaben, H. Weyhers, F. Specht, J. S. Lucks, Cytotoxicity of magnetite-loaded polylactide, polylactide/glycolide particles and solid lipid nanoparticles, Int. J. Pharm. 138 (1) (1996) 85-94). The PACA polymers are non-polar and more effective at entrapping hydrophobic compounds within the nanoparticles matrix, and reportedly degrade rapidly. However, toxicity in human fibroblasts due to byproducts resulting from degradation of the PACA backbone has been reported (C. Lherm, R. H. Müller, F. Puisieux, P. Couvreur, Alkylcyanoacrylate drug carriers: II. Cytotoxicity of cyanoacrylate nanoparticles with different alkyl chain length, Int. J. Pharm. 84 (1) (1992) 13-22).

Polystyrene nanoparticles have also been investigated, and likewise found to entrap lipophilic compounds to a greater extent compared to poly(hydroxy acids) nanoparticles (D. A. Norris, N. Puri, M. E. Labib, P. J. Sinko, Determining the absolute surface hydrophobicity of microparticulates using thin layer wicking, J. Control. Release 59 (2) (1999) 173-185; M. C. Venier-Julienne, J. P. Benoit, Preparation, purification and morphology of polymeric nanoparticles as drug carriers, Pharm. Acta Helv. 71 (2) (1996) 121-128). This can be attributable to their more hydrophobic nature, which may be reinforced by aromatic interactions between pairs of benzene rings in polystyrene (J. W. Longworth, F. A. Bovey, Conformations and interactions of excited states. I. Model compounds for polymers, Biopolymers 4 (10) (1966) 1115-1129). The higher encapsulation of polystyrene nanoparticles could be also attributed to stabilizing $\pi$-$\pi$ interactions between its phenyl groups and heteroaromatic compounds (K. Lee, J. Hong, Nonionic adsorption of aromatic amino acids on a cation-exchange resin, React. Funct. Polym. 28 (1) (1995) 75-80).

While the prior art nanoparticles can efficiently entrap lipophilic compounds, there are still problems with the nanoparticles degrading and producing by-products that may affect biological structures. Additionally, some of the prior art nanoparticles degrade very rapidly thus flooding the subject with the pharmaceutical agent encapsulated within the nanoparticle. A slow controlled release is not possible with the nanoparticles of the prior art. Given the shortcomings of the prior art, what is needed is a chemically-stable biochemically-degradable nanoparticle that can efficiently entrap lipophilic substrates.

SUMMARY OF INVENTION

A long-felt but unfulfilled need exists for new chemically-stable, biochemically-degradable nanoparticles for delivery of pharmaceutical agents such as imaging compounds, antibiotics, and anticancer drugs.

The present invention comprises poly(vinyl benzoate) nanoparticle suspensions as molecular carriers. These nanoparticles are formed by nanoprecipitation of poly(vinyl benzoate) in water using Pluronic F68 as surfactant to create spherical nanostructures measuring about 200-250 nm in diameter. These nanoparticles are stable in phosphate buffer and blood serum, and only slowly degrade in the presence of esterases. Pluronic F68 stabilizes the nanoparticle and also protects it from enzymatic degradation.

Up to 1.6% by weight of a lipid-soluble molecule such as coumarin-6 can be introduced into the nanoparticle during nanoprecipitation, compared to a water-soluble compound (5(6)-carboxyfluorescein) which gave almost no loading. Kinetics experiments in phosphate buffer indicate that 78% of the coumarin-6 was encapsulated within the polymer matrix of the nanoparticle, and the residual 22% of coumarin-6 was surface-bound and quickly released.

The nanoparticles are non-toxic in vitro towards human epithelial cells ($IC_{50}$>1000 μg/mL) and primary bovine primary aortic endothelial cells ($IC_{50}$>500 μg/mL), and exert a non-observable bactericidal activity against a selection of representative test microbes (MIC>250 μg/mL). Poly(vinyl benzoate) nanoparticles are suitable carriers for molecular delivery of lipophilic small molecules such as drugs, pharmaceuticals, and imaging agents.

In an embodiment, a composition of nanoparticles is presented comprising: at least one nanoparticle formed from poly(vinyl benzoate) and at least one surfactant; a pharmaceutically acceptable carrier; and a lipophilic molecule. The surfactant can be a pluronic such as Pluronic F68. The at least one nanoparticle may have a mean particle size of between about 50 nm and about 350 nm or between about 200 nm and about 250 nm. The size of the lipophilic molecule may be up to about 5% by weight. The lipophilic molecule may be an antibacterial agent or drug.

In another embodiment, an in vivo molecular carrier is presented comprising a poly(vinyl benzoate) nanoparticle suspension. The nanoparticle suspension may be formed using Pluronic F68 as a surfactant. The molecular carrier may encapsulate a lipophilic small molecule.

In a further embodiment, a method of generating a small molecular drug carrier is presented comprising: nanoprecipitation of a polymer, further comprising: adding at least one surfactant to water, where the at least one surfactant is pluronic F68; dissolving or diluting poly(vinyl benzoate) in acetone; dissolving a predetermined quantity of lipid-soluble molecule in the acetone; adding the poly(vinyl benzoate)-acetone solution to the water to form a mixture of pluronic F68 and poly(vinyl benzoate); stirring the mixture of pluronic F68 and poly(vinyl benzoate); and evaporating the acetone from the mixture of pluronic F68 and poly(vinyl benzoate) to leave a suspension of polyvinyl benzoate nanoparticles.

The poly(vinyl benzoate) can be added at about 0.5% (w/v) to the acetone. The Pluronic F68 can be added at about 0.5% w/v. The acetone can be evaporated overnight at room temperature.

The polyvinyl benzoate nanoparticles can be washed by: centrifuging the suspension of polyvinyl benzoate nanoparticles at 10,000 rpm for 10 minutes; resuspending the pellet formed from the centrifugation in distilled water; and sonicating the pellet for 1 minute to disperse any aggregates.

The nanoparticles may be frozen at −70° C.; and lyophilized for 24 hours.

Another embodiment of the present invention is a method of delivering a small molecule to a subject comprising: administering a therapeutically effective amount of a nanoparticle suspension to a subject in need thereof wherein the nanoparticle suspension is formed of poly(vinyl benzoate) and Pluronic F68. The small molecule may be lipophilic.

BRIEF DESCRIPTION OF THE DRAWINGS

For a fuller understanding of the invention, reference should be made to the following detailed description, taken in connection with the accompanying drawings, in which.

DETAILED DESCRIPTION OF THE PREFERRED EMBODIMENT

In the following detailed description of the preferred embodiments, reference is made to the accompanying drawings, which form a part hereof, and within which are shown by way of illustration specific embodiments by which the invention may be practiced. It is to be understood that there are other embodiments by which the invention may be practiced. It is to be understood that other embodiments may be utilized and structural changes may be made without departing from the scope of the invention.

All numerical designations, such as pH, temperature, time, concentration, and molecular weight, including ranges, are approximations which are varied up or down by increments of 1.0 or 0.1, as appropriate. It is to be understood, even if it is not always explicitly stated that all numerical designations are preceded by the term "about". It is also to be understood, even if it is not always explicitly stated, that the reagents described herein are merely exemplary and that equivalents of such are known in the art and can be substituted for the reagents explicitly stated herein.

Concentrations, amounts, solubilities, and other numerical data may be expressed or presented herein in a range format. It is to be understood that such a range format is used merely for convenience and brevity and thus should be interpreted flexibly to include not only the numerical values explicitly recited as the limits of the range, but also to include all the individual numerical values or sub-ranges encompassed within that range as if each numerical value and sub-range is explicitly recited. As an illustration, a numerical range of "about 1 to about 5" should be interpreted to include not only the explicitly recited values of about 1 to about 5, but also include the individual values and sub-ranges within the indicated range, to the tenth of the unit. Thus, included in this numerical range are individual values such as 2, 3, and 4 and sub-ranges such as from 1-3, from 2-4 and from 3-5, etc. This same principle applies to ranges reciting only one numerical value. Furthermore, such an interpretation should apply regardless of the range or the characteristics being described.

The term "about" or "approximately" as used herein refers to being within an acceptable error range for the particular value as determined by one of ordinary skill in the art, which will depend in part on how the value is measured or determined, i.e. the limitations of the measurement system, i.e. the degree of precision required for a particular purpose, such as a pharmaceutical formulation. For example, "about" can mean within 1 or more than 1 standard deviation, per the practice in the art. Alternatively, "about" can mean a range of up to 20%, preferably up to 10%, more preferably up to 5% and more preferably still up to 1% of a given value. Alternatively, particularly with respect to biological systems or processes, the term can mean within an order of magnitude, preferably within 5-fold, and more preferably within 2-fold, of a value. Where particular values are described in the application and claims, unless otherwise stated, the term "about" meaning within an acceptable error range for the particular value should be assumed.

As used in the specification and claims, the singular forms "a", "an" and "the" include plural references unless the context clearly dictates otherwise. For example, the term "a nanoparticle" includes a plurality of nanoparticles, including mixtures thereof.

The term "composition" as used herein encompasses a product comprising the specified ingredients in the specified amounts, as well as any product which results, directly or indirectly, from combination of the specified ingredients in the specified amounts.

The term "stabilizer" and "surfactant" are used interchangeably herein and refers to any substance, i.e. a surface active substance, capable of stabilizing a nanoparticle or an emulsion for preparing a nanoparticle. For example, pluronics may be used as surface active substances (surfactants).

The term "nanoparticle" as used herein refers to a particle or structure which is biocompatible with and sufficiently resistant to chemical and/or physical destruction by the environment of such use so that a sufficient number of the nanoparticles remain substantially intact after delivery to the site of application or treatment and whose size is in the nanometer range. For the purposes of the present invention, a nanoparticle typically ranges between about 1 nm to about 1000 nm, preferably between about 50 nm and about 500 nm, more preferably between about 50 nm and about 350 nm, more preferably between about 200 nm and about 250 nm. The terms "nanoparticle" and "nanostructure" are used interchangeably herein.

The term "nanoprecipitation" as used herein refers to the process of forming nanoparticles through solvent displacement. In nanoprecipitation, preformed polymers are converted into nanoparticles by dissolving the polymer in a water-miscible organic solvent and adding this solution to water containing a suitable surfactant. Generally, here, a solution of poly(vinyl benzoate) was prepared in acetone and was introduced into an aqueous solution containing known concentrations of a surfactant such as Pluronic F68 under magnetic stirring.

The term "lipophilic small molecule" as used herein refers to compounds which dissolve in lipids, fats, oils and non-polar solvents. The lipophilic small molecule may be a pharmaceutically active agent, drug, imaging agent, therapeutic agent, diagnostic agent, compound, or composition. The lipophilic small molecule may comprise up to about 5% by weight of the nanoparticle composition.

The term "drug" as used herein refers to a chemical entity of varying molecular size, small and large, naturally occurring or synthetic, that exhibits a therapeutic effect in animals and humans. A drug may include, but is not limited to, a therapeutic protein, peptide, antigen, or other biomolecule.

The term "pluronics" as used herein refers to a type of stabilizer that may be used during nanoparticle synthesis as an emulsion. Pluronics prevent the adsorption of opsonins onto the particle surface (opsonization). The anti-opsonic effect of this emulsifier enhances the blood circulation time of the nanoparticles considerably, which make them suitable for intravenous injection. In addition, pluronics reportedly increase the uptake of pharmacologically active molecules through biological membranes.

The term "degradation" as used herein refers to becoming soluble, either by reduction of molecular weight (as in the case of a polyester) or by conversion of the hydrophobic groups to hydrophilic groups (as in the case of PPS).

The term "pharmaceutically active agent" as used herein refers to a molecule, a group of molecules, a complex or substance that is administered to a subject for diagnostic, therapeutic, preventative, medical, or veterinary purposes and includes drugs and vaccines. Included are externally and internally administered topical, localized and systemic human and animal pharmaceuticals, treatments, remedies, nutraceuticals, cosmeceuticals, biologicals, and diagnostics, including preparations useful in clinical and veterinary screening, prevention, prophylaxis, healing, wellness, detection, imaging, diagnosis, therapy, surgery, monitoring, cosmetics, forensics, and the like. The pharmaceutically active agents are preferably lipophilic for encapsulation within the nanoparticles of the present invention.

The term "polymer" as used herein refers to a relatively high molecular weight organic compound, natural or synthetic, whose structure can be represented by a repeated small unit, the monomer. Synthetic polymers are typically formed by addition or condensation polymerization of monomers. The polymers used or produced in the present invention are biodegradable. The polymer is suitable for use in the body of a subject, i.e. is biologically inert and physiologically acceptable, non-toxic, and is biodegradable in the environment of use, i.e. can be resorbed by the body.

The term "copolymer" as used herein refers to a polymer formed from two or more different repeating units (monomer residues).

A "pharmaceutically acceptable carrier" as used herein is defined as any of the standard pharmaceutically acceptable carriers. The pharmaceutical compositions of the subject invention can be formulated according to known methods for preparing pharmaceutically useful compositions. The pharmaceutically acceptable carrier can include diluents, adjuvants, and vehicles, as well as carriers, and inert, non-toxic solid or liquid fillers, diluents, or encapsulating material that does not react with the active ingredients of the invention. Examples include, but are not limited to, phosphate buffered saline, physiological saline, water, and emulsions, such as oil/water emulsions. The carrier can be a solvent or dispersing medium containing, for example, ethanol, polyol (for example, glycerol, propylene glycol, liquid polyethylene glycol, and the like), suitable mixtures thereof, and vegetable oils. Formulations are described in a number of sources that are well known and readily available to those skilled in the art. For example, *Remington's Pharmaceutical Sciences* (Martin E W [1995] Easton Pa., Mack Publishing Company, 19$^{th}$ ed.) describes formulations which can be used in connection with the subject invention.

The term "administration" as used herein refers to the delivery of a composition of nanoparticles to an appropriate location of the subject or in vitro to which a desired effect is achieved. Routes of administration include, but are not limited to, intravenous, intra-arterial, intracutaneous, topical, rectal, vaginal, buccal, inhalation, ocular, and oral.

The "therapeutically effective amount" for purposes herein is thus determined by such considerations as are known in the art. A therapeutically effective amount of the nanoparticles of the present invention is that amount necessary to provide a therapeutically effective result in vivo. The amount of nanoparticles must be effective to achieve a response, including but not limited to total prevention of (e.g., protection against) and to improved survival rate or more rapid recovery, or improvement or elimination of symptoms associated with a given disorder or other indicators as are selected as appropriate measures by those skilled in the art. In accordance with the present invention, a suitable single dose size is a dose that is capable of preventing or alleviating (reducing or eliminating) a symptom in a patient when administered one or more times over a suitable time period. One of skill in the art can readily determine appropriate single dose sizes for systemic administration based on the size of a mammal and the route of administration.

The preparation and properties of poly(vinyl benzoate) nanoparticle suspensions as molecular carriers are described for the first time. These nanoparticles can be formed by nanoprecipitation of commercial poly(vinyl benzoate) in water using Pluronic F68 as surfactant, to create spherical nanostructures measuring about 200-250 nm in diameter. These nanoparticles are stable in phosphate buffer and blood serum, and only slowly degrade in the presence of esterases. Pluronic F68 stabilizes the nanoparticle and also protects it from enzymatic degradation. Up to about 1.6% by weight of a lipid-soluble molecule such as coumarin-6 can be introduced into the nanoparticle during nanoprecipitation, compared to a water-soluble compound (5(6)-carboxyfluorescein) which gave almost no loading. Kinetics experiments in phosphate buffer indicate that about 78% of the coumarin-6 was encapsulated within the polymer matrix of the nanoparticle, and the residual about 22% of coumarin-6 was surface-bound and quickly released. The nanoparticles are non-toxic in vitro towards human epithelial cells (IC50N1000 μg/mL) and primary bovine aortic endothelial cells (IC50N500 μg/mL), and non-bactericidal against a selection of representative test microbes (MIC N250 μg/mL). These properties suggest that the poly(vinyl benzoate) nanoparticles may be suitable carriers for molecular delivery of lipophilic small molecules such as pharmaceutical and imaging agents.

Figure 1:
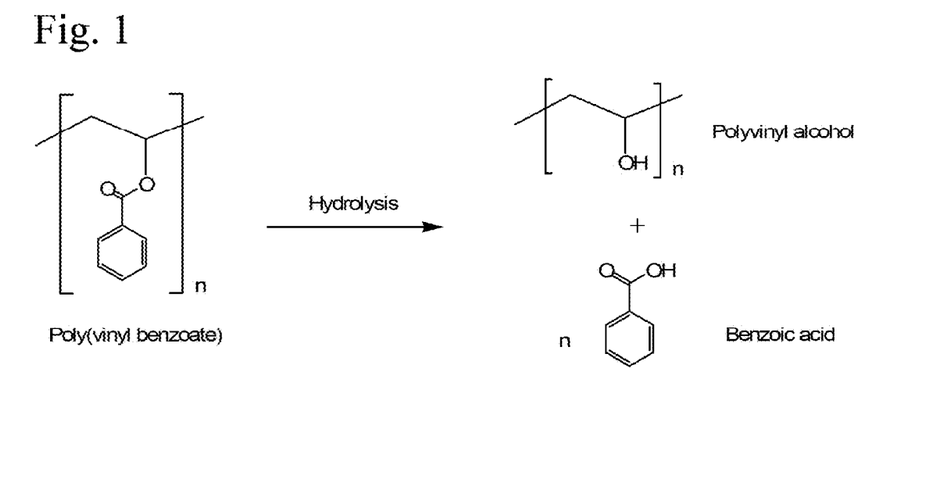
FIG. 1 is a diagram of poly(vinyl benzoate) and its hydrolysis products.

Given the prior art relating to nanoparticles, the inventors sought to develop poly(vinyl benzoate) nanoparticles that, like polystyrene nanoparticles, could efficiently entrap lipophilic substrates (such as drug molecules) (T. Hirose, K. Mizoguchi, Y. Kamiya, Gas transport in poly(vinyl benzoate), J. Appl. Poly. Sci. 30 (1) (1985) 401-410) while having the potential to bioerode by lateral chain cleavage similar to that of PACA, but giving non-toxic by-products (polyvinyl alcohol and benzoic acid) (FIG. 1).

In this report the methodology for the formation of poly(vinyl benzoate) nanoparticles is described, along with an investigation into their aqueous stability and enzymatic degradability. These nanoparticles were prepared by the nanoprecipitation method affording stable aqueous suspensions of polymeric nanospheres in one step (H. Fessi, F. Puisieux, J. P. Devissaguet, N. Ammoury, S. Benita, Nanocapsule formation by interfacial polymer deposition following solvent displacement, Int. J. Pharm. 55 (1) (1989) R1-4). Phluronic F68 was incorporated in the aqueous phase as a co-emulsifier in the nanofabrication process. This surfactant presents numerous advantages as a surface coating agent for nanoparticle-based drug delivery. The hydrophilic layer of pluronic prevents the adsorption of opsonins onto the particle surface (opsonization) and therefore should prevent rapid clearance by the macrophages in the reticuloendothelial system (RES), especially in the spleen and in the liver. The anti-opsonic effect of this emulsifier enhances the blood circulation time of the nanoparticles considerably, which make them suitable for intravenous injection (D. E. Owens III, N. A. Peppas, Opsonization, biodistribution, and pharmacokinetics of polymeric nanoparticles, Int. J. Pharm. 307 (1) (2006) 93-102). In addition, pluronics reportedly increase the uptake of pharmacologically active molecules through biological membranes (E. Jeon, H. D. Kim, J. S. Kim, Pluronic-grafted poly-(L)-lysine as a new synthetic gene carrier, J. Biomed. Mater. Res. 66A (4) (2003) 854-859), and have been approved by the U.S. Food and Drug Administration for medical applications.

Figure 2:
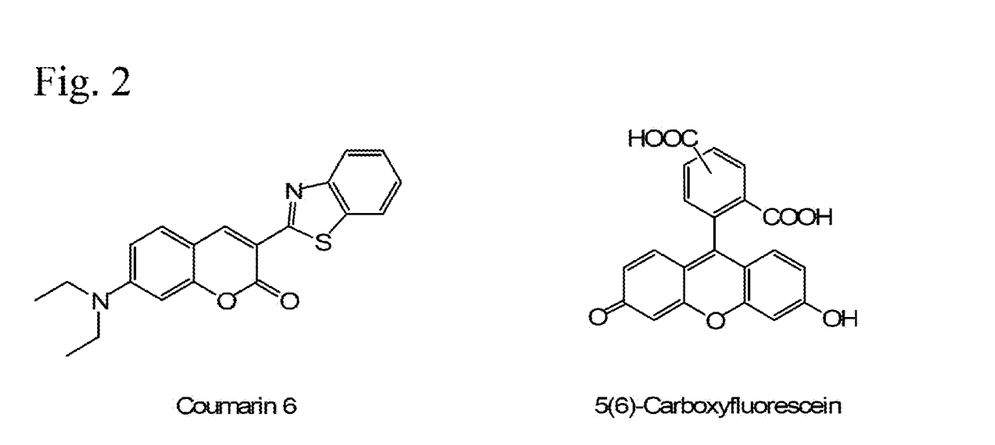
FIG. 2 is a diagram showing test fluorophores used.

In order to analyze the nanoparticulate system for potential application in sustained drug release, the particle size and their surface charge properties were measured by dynamic light scattering and their surface morphology was characterized by scanning electron microscopy. Fluorescent probes, coumarin-6 and 5(6)-carboxyfluorescein (FIG. 2), as hydrophobic and hydrophilic drug models, respectively, were also used to encapsulate inside the poly(vinyl benzoate) matrix. The drug content and loading efficiency for each compound was then determined. The mechanism of biodegradation was further studied by enzymatic degradation and the released benzoic acid was used as the marker of erosion. Following this, the in vitro stability of the nanoparticles in serum was assayed to evaluate their potential for systemic applications.

Materials and Methods

Poly(vinyl benzoate) (average molecular weight 20,000-70,000) was obtained from Monomer-Polymer and Dajac Labs, Inc. (Feasturville, Pa.). Acetone, dimethyl sulfoxide (DMSO), methanol, dichloromethane, ethanol, phosphate buffered saline (PBS), coumarin-6, 5(6)-carboxyfluorescein, benzoic acid, vinyl benzoate, Pluronic F68, Tween 80, rat blood serum and esterase from porcine liver (E.C. 232-77-7) were purchased from Sigma-Aldrich (St. Louis, Mo.). Trifluoroacetic acid (TFA), acetonitrile and water for chromatographic analysis were HPLC grade from Sigma-Aldrich as well. Potassium hydroxide was procured from Fisher Scientific (Fair Lawn, N.J.) and pig liver esterase was supplied by Lee Biosolutions, Inc. (St. Louis, Mo.).

The nanoparticles were prepared by the nanoprecipitation method using solvent displacement as reported earlier (H. Fessi, F. Puisieux, J. P. Devissaguet, N. Ammoury, S. Benita, Nanocapsule formation by interfacial polymer deposition following solvent displacement, Int. J. Pharm. 55 (1) (1989) R1-4). Briefly, a solution of poly(vinyl benzoate) was prepared in acetone and was introduced into an aqueous solution containing known concentrations of Pluronic F68 under magnetic stirring. The rate of addition of organic phase to aqueous phase, volume ratios and the stirring speed were optimized to ensure batch-to-batch reproducibility. Typically, a 0.5% (w/v) solution of poly(vinyl benzoate) in 20 mL of acetone was introduced into an aqueous solution of Pluronic F68 (40 ml at 0.5% w/v). The rate of addition was controlled through a syringe pump at about 1 mL/min and stirring was maintained at a speed that facilitated formation of a vortex in the solution. The acetone was evaporated overnight under stirring at room temperature to leave a suspension of polyvinyl benzoate nanoparticles. The suspension of nanoparticles was centrifuged at 10,000 rpm for 10 minutes (Eppendorf Centrifuge 5424), and the resulting pellet was resuspended in distilled water and sonicated for 1 minute to disperse any aggregates. Centrifugation was repeated two more times at 10,000 rpm to remove the excess Pluronic F68. After the final centrifugation, the nanoparticles were resuspended in 10 mL of distilled water and sonicated for 2 minutes. The suspension was then frozen at −70° C. and subsequently lyophilized for 24 hours. The lyophilized nanoparticles were stored desiccated as a dried white powder at room temperature. Drug-loaded nanoparticles were prepared by pre-dissolving a known quantity (typically about 2 mg) of coumarin-6 or 5(6)-carboxyfluorescein in acetone containing the poly(vinyl benzoate) before introduction into aqueous medium.

To determine the physical properties of the polyvinyl benzoate nanoparticles, freeze-dried samples of the nanoparticles were dispersed in deionized water and sonicated for 5 minutes. Measurements were made by dynamic laser light scattering (DLS) using a Malvern Nano ZS instrument. Analysis was performed in triplicate and results are expressed as the mean volumetric diameter. Zeta potential measurements were done by micro-electrophoresis on the same instrument. For each sample, the average of twelve determinations was reported.

Surface morphology of the polyvinyl benzoate nanoparticles was observed by scanning electron microscopy on a Hitachi S800 SEM instrument. Samples were prepared by placing a drop of the re-dispersed nanoparticles (~10 μg/mL) on a silicon wafer and allowing the water to evaporate at room temperature for approximately 12 hours.

To determine the entrapment content and loading efficiency, nanoparticle samples loaded with coumarin-6 or 5(6)-carboxyfluorescein were prepared as follows: 1 mg of polyvinyl benzoate nanoparticle was dissolved in 1 mL of dichloromethane and this mixture was stirred for 5 hours to swell the nanoparticles and release the entrapped molecule (fluorophore). This solution was left for evaporation and the residue was then solubilized in 1 ml of acetonitrile. High performance liquid chromatography (HPLC) was done on a Shimadzu Prominence system with a reverse-phase Shimadzu column (C18, 0.46×5 cm). Samples were eluted using a gradient from 100% of a 10 mM PBS solution (pH 7.4) to 100% of acetonitrile in 10 minutes at a flow rare of 1 mL/minute. The detection was performed using a Shimadzu SPD-20A UV-visible detector at 444 nm (coumarin-6) or at 492 nm (5(6)-carboxyfluorescein). The concentration of the fluorescent probe was determined by comparison to known concentrations of each reference compound (using standardized curves). The amount of entrapment of coumarin-6 or 5(6)-carboxyfluoroscein in the nanoparticles and their overall loading efficiencies were calculated as follows:

Entrapment content=mass of fluorescent probe in nanoparticles/mass of recovered nanoparticles×100

Loading efficiency=mass of fluorescent probe in nanoparticles/mass of fluorescent probe used in the formulation×100

In Vitro Release Study

The profile for release of the fluorophore in each sample was obtained by dispersing 2 mg of coumarin-6 or 5(6)-carboxyfluorescein-loaded nanoparticles in 1 mL of PBS (pH 7.4) containing 0.1% (w/v) of Tween 80 in a centrifuge tube. The suspensions were stirred magnetically at 150 rpm for 96 hours with a constant temperature of 37° C. Tween 80 was added to the suspension to ensure sink conditions as reported elsewhere (Y. Dong, S.-S. Feng, Poly(D, L-lactide-co-glycolide) (PLGA) nanoparticles prepared by high pressure homogenization for paclitaxel chemotherapy, Int. J. Pharm. 342 (1-2) (2007) 208-214). At designated time intervals, the samples were centrifuged at 10,000 rpm for 5 minutes, the supernatant was withdrawn and the same amount of fresh medium was added. The percentage of fluorescent probe released into the supernatant was determined by HPLC as previously described in 2.5, and the amount of coumarin-6 released was then correlated to the amount entrapped before and after in vitro release.

Nanoparticle Polymer Degradation Experiments in Presence of Esterases

To study potential degradation properties of the nanoparticle samples, 1 mg of purified, lyophilized poly(vinyl benzoate) nanoparticles (unloaded) was reconstituted in 1 mL of PBS (pH 7.4) containing 100 U/mL of pig liver esterase. Three identical samples at three different concentrations (100 μg/mL, 500 μg/mL, 1 mg/mL) were incubated at 37° C. for 32 days. Every 24 hours, each batch was centrifuged to separate the supernatant from the nanoparticles and fresh medium containing 100 U/mL of pig liver esterase was added. The enzymatic cleavage of the ester bonds of the poly(vinyl benzoate) backbone causes the release of benzoic acid and polyvinyl alcohol, which was followed and the data plotted in FIG. 5. The UV-detectable benzoic acid was used as an indicator of bioerosion and its concentration was determined by HPLC. For this chromatographic experiment, the UV detection was performed at 235 nm and the elution was done with a gradient from 100% of 0.5% (v/v) aqueous TFA solution to 100% of acetonitrile. The percentage of degradation is expressed as a percentage of benzoic acid release. The theoretical full release of benzoic acid was determined by total erosion of 1 mg/mL of poly(vinyl benzoate) nanoparticles in 1N potassium hydroxide in methanol. Benzoic acid concentration was established by using a calibration curve.

The degradation of the poly(vinyl benzoate) in the presence of pig liver esterase was also investigated as a control. The procedure used was as described above and the experiment was extended to 14 days. It was observed that after two weeks in the presence of the esterase, no notable difference of this sample compared to the poly(vinyl benzoate) nanoparticles made without Pluronic F68 surfactant.

Stability of the Poly(Vinyl Benzoate) Nanoparticles in Blood Serum

To evaluate their stability and simulate their fate in the case of intravenous administration, lyophilized nanoparticles made with Pluronic F68 were suspended in deionized water and then added to rat blood serum at a final concentration of 1 mg/mL in a water/serum ratio of 1/4 (v/v). Three suspensions were kept at 37° C. with magnetic stirring. After 1, 3 and 8 days the nanoparticle samples were washed twice with deionized water by centrifugation at 10,000 rpm for 5 minutes. The remaining pellets were submitted to SEM analysis.

Microbiological Assays

Each of the nanoparticle samples were examined for antimicrobial activity by testing against Staphylococcus aureus (ATCC 25923) and E. coli K12 (ATCC 23590) by Kirby-Bauer antimicrobial susceptibility testing on agar plates and by determination of minimum inhibitory concentration values by agar serial dilution. These procedures were adapted directly from NCCLS protocols (National Committee for Clinical Laboratory Standards, Methods for dilution antimicrobial susceptibility tests for bacteria that grow aerobically-sixth edition (2003): Approved Standard M7-A6, 15, NCCLS, Wayne, Pa., USA).

Kirby-Bauer Antimicrobial Susceptibility Testing:

From a freezer stock in tryptic soy broth (Difco Laboratories, Detroit, Mich.) and 20% glycerol, a culture of each microorganism was grown on tryptic soy agar (TSA) plates (Becton-Dickinson Laboratories, Cockeysville, Md.) at 37° C. for 24 hours. A $10^8$ suspension was then made in sterile phosphate buffered saline (pH 7.4) and swabbed across fresh TSA plates. Four equidistantly-spaced circular wells (6 mm in diameter) were cut into the inoculated plates and 20, 50, or 100 μL volumes of a 1 mg/mL stock solution of the test compound in DMSO was pipetted into the wells. 10 μL of a 1 mg/mL solution of penicillin G in sterile phosphate buffered saline (PBS) was added to the fourth well (as a control). The plates were covered and then incubated for 24 hours at 37° C. Antimicrobial susceptibilities were determined by measuring the diameter (in mm) of any cleared circular zones of growth inhibition appearing around each well.

Determination of Minimum Inhibitory Concentration (MIC) by Agar Serial Dilution Assays:

Sample tests were performed in 24-well plates (Costar 3524, Cambridge, Mass.) by adding known concentrations of the nanoparticle suspensions to Mueller-Hinton II agar (Becton-Dickinson Laboratories, Cockeysville, Md.) for a total volume of 1 mL in each well. The final concentrations of solid nanoparticles used in each line of wells were 256, 128, 64, 32, 16, 8, and 4 μg/mL. Following the preparation of the well plates, the media was allowed to solidify at room temperature for 24 hours before incubation. From a 24-hour culture of each microorganism on TSA plates, the test bacterial strains were grown overnight in 5 mL of tryptic soy broth at 37° C. to $10^7$ CFU/mL as monitored by optical density measurement at 600 nm on a Bio-Tek Biomate 3 spectrophotometer. 1 μL of each culture was then applied to the appropriate well of agar and incubated at 37° C. overnight. After 24 h, the wells were examined for growth. The MIC value is defined as the lowest concentration (in μg/mL) where there was no visible growth of bacteria in the wells.

In Vitro Cytotoxicity Testing

In Vitro Testing Against Epithelial Cells:

Human epithelial cells (HaCaT) from Lonza Walkersville, Inc were grown in culture medium (Dulbecco's Modified Eagle Medium (DMEM) containing 10% (v/v) fetal bovine serum (FBS) and 50 □g/mL gentamycin) at 37° C. with a 5% $CO_2$ atmosphere for several days until cells were confluent. The cells were harvested and re-suspended in DMEM containing 10% (v/v) fetal bovine serum (FBS) and 0.1% (w/v) gentamycin. The cells were counted using a hemocytometer, the total number of cells was determined and the cells were seeded into 96-well plates at 50,000 cells per well. Each well contained 150 μL DMEM with 10% (v/v) FBS and 0.1% (w/v) gentamycin. Cells were allowed to grow for 24 hours prior to treatment with the nanoparticles suspensions. Testing of each dispersion at different concentrations (1, 0.5, 0.25, 0.125 mg/mL) was performed in triplicate. The plates were then incubated at 37° C. and observed under the microscope at various time points. After 48 hours, 15 μL of a 5 mg/mL solution of 3-(4,5-dimethyl-2-thiazolyl)-2,5-diphenyltetrazolium bromide (MTT) in phosphate buffered saline (10% of the total culture volume) was added to each well. The plates were incubated for 4 hours to allow sufficient time for the conversion of the MTT dye (yellow liquid) to the water-insoluble formazan derivative, 1-(4,5-dimethylthiazol-2-yl)-3,5-diphenylformazan (purple solid) by the mitochondrial dehydrogenases in the living cells. After incubation, purple crystals were observed and the media was removed from each well by aspiration. The crystals were then dissolved by adding 100 μL of DMSO to each well. DMSO was also added to the wells designated as reference blanks. Viable cell count was determined spectrophotometrically using a microplate reader by measuring the absorbance at two discrete wavelengths (595 and 630 nm). For each dispersion at each concentration, the absorbance values were averaged and the percent cell viability was determined as a percentage of the average absorbance obtained from the untreated cells.

In Vitro Testing Against Endothelial Cells:

Primary bovine aortic endothelial cells and EBM-2 cell culture medium were obtained from Lonza Walkersville, Inc. Cells were maintained in culture medium supplemented with 10% FBS and 100 IU penicillin/100 μg/mL streptomycin sulfate in a humidified incubator containing 5% $CO_2$ at 37° C. For cytotoxicity testing, cells were trypsinized, counted, centrifuged at 120 g, and resuspended in fresh culture medium. Cells were plated in a volume of 100 mL ($2.5 \times 10^4$ cells/well) in 96-well flat-bottom culture dishes. After 16-18 h of incubation, 100 μL of medium or medium containing test samples was added to each well. Testing of each dispersion at different concentrations (1, 0.5, 0.25, 0.125 μg/mL) was performed in triplicate. After 48 h, 20 μL of MTT (1.25-4 mg/mL in DPBS) was added to each well, and the cells were further incubated for 2-3.5 h. The medium was aspirated, and the formazan product generated in each well was dissolved in 100 μL of DMSO. Plates were read in a BioTek Synergy 2 SLFA plate reader set at 540 nm (background subtract at 660 nm). Cell viability was calculated as a percentage of the control sample (sample absorbance/control medium absorbance×100).

Formation and Characterization of Poly(Vinyl Benzoate) Nanoparticles

Research has recently focused on the preparation and studies of nanoparticle-bound antibiotics for controlling the growth of certain pathogenic bacteria, including methicillin-resistant *Staphylococcus aureus* (MRSA) and *Bacillus anthracis* (E. Turos, J.-Y. Shim, Y. Wang, K. Greenhalgh, G. S. K. Reddy, S. Dickey, D. V. Lim, Antibiotic-conjugated polyacrylate nanoparticles: new opportunities for development of anti-MRSA agents, Bioorg. Med. Chem. Lett. 17 (1) (2007) 53-56; E. Turos, G. S. K. Reddy, K. Greenhalgh, P. Ramaraju, S. C. Abeylath, S. Jang, D. V. Lim, Penicillin-bound polyacrylate nanoparticles: restoring the activity of β-lactam antibiotics against MRSA, Bioorg. Med. Chem. Lett. 17 (12) (2007) 3468-3472; S. C. Abeylath. E. Turos, Glycosylated polyacrylate nanoparticles by emulsion polymerization, Carb. Polym. 70 (1) (2007) 32-37; S. C. Abeylath, E. Turos, S. Dickey. D. V. Lim, Glyconanobiotics: novel carbohydrated nanoparticle antibiotics for MRSA and *Bacillus anthracis*, Bioorg. Med. Chem. 16 (5) (2008) 2412-2418; J. Garay-Jimenez, A. Young, D. Gergeres, E. Turos, Methods for purifying and detoxifying sodium dodecyl sulfate-stabilized polyacrylate nanoparticles, Nanomed: Nanotech. Biol. Med. 4 (2) (2008) 98-105). Prior investigations have all centered on polyacrylate nanoparticles prepared as an aqueous emulsion by free-radical polymerization in water. Sodium dodecyl sulfate is a typical surfactant for this, although other tensoactive agents can be used (J. Garay-Jimenez, D. Gergeres, A. Young, S. Dickey, D. V. Lim, E. Turos. Physical properties and biological activity of poly(butyl acrylate-styrene) nanoparticle emulsions prepared with conventional and polymerizable surfactants, Nanomed: Nanotech. Biol. Med. 5 (4) (2009) 443-451).

One of the goals is to develop suitable nanoparticle systems to protect and deliver antibiotic agents to sites of infection, where they can act directly on the microbe (K. Greenhalgh, E. Turos, In viva studies of polyacrylate nanoparticle emulsions for topical and systemic applications, Nanomed: Nanotech. Biol. Med. 5 (1) (2009) 46-54). A previous investigation reported on the formulation of poly(butyl acrylate-styrene) nanoparticles as an antibiotic delivery system, altering the types of monomers and surfactants used to induce changes in particle characteristics and antibacterial properties. It was desirable to extend those experiments toward the design of polymeric nanoparticles that could not only carry potentially chemically labile antibiotics, but also might be able to undergo degradation to release the entrapped molecule. Thus, the starting point was to replace the butyl acrylate-styrene monomers used to make the nanoparticles by emulsion polymerization with a different, potentially biodegradable variant, such as vinyl benzoate. Attempts to prepare stable suspensions of poly(vinyl benzoate) under previously defined emulsion polymerization conditions (E. Turos, J.-Y. Shim, Y. Wang, K. Greenhalgh, G. S. K. Reddy, S. Dickey, D. V. Lim, Antibiotic-conjugated polyacrylate nanoparticles: new opportunities for development of anti-MRSA agents, Bioorg. Med. Chem. Lett. 17 (1) (2007) 53-56) using 3 weight % of sodium dodecyl sulfate (SDS) as an emulsifying agent, were unsuccessful. The use of Pluronic F68 as the surfactant was changed, resulting in the formation of nanoparticles with a mean diameter of 40 nm and a zeta potential of approximately −20 mV. Unfortunately, these nanoparticle emulsions were not stable after purification by centrifugation or dialysis. Consequently, alternative means for forming nanoparticles were analyzed based on the poly(vinyl benzoate) matrix, and the nanoprecipitation method was investigated. With this technique, preformed polymers are converted into nanoparticles by dissolving the polymer in a water-miscible organic solvent and adding this solution to water containing a suitable surfactant.

Acetone was used as the solvent for the polymer, and satisfactory results were obtained with Pluronic F68. Nanoparticles were also formed without using an added surfactant in order to study the influence of Pluronic F68 on the degradation properties of the nanoparticles. Other solvents that may be used in the present invention include, but are not limited to, hardly water-soluble organic solvents having a low boiling point such as halogenated alkanes, methanol, ethanol, ethyl acetate, diethyl ether, cyclohexane, benzene, and toluene.

Figure 3:
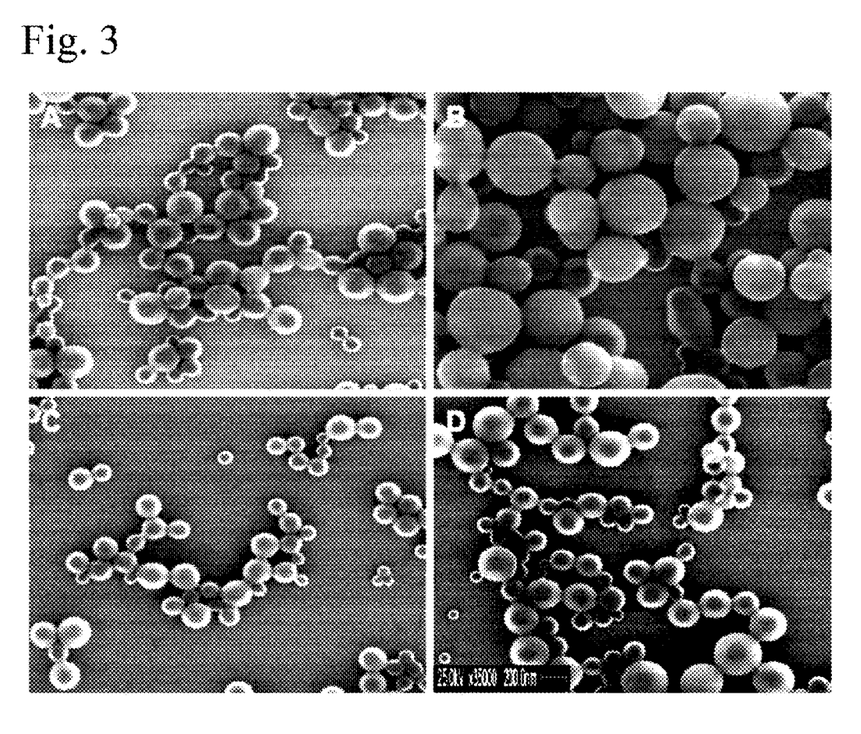
FIG. 3 shows SEM micrographs of poly(vinyl benzoate) nanoparticles prepared with Pluronic-F68 (image A) and without Pluronic-F68 (image B). SEM micrographs of Pluronic-F68-coated poly(vinyl benzoate) nanoparticles loaded with coumarin-6 (image C) and 5(6)-carboxyfluorescein (image D).

The physical characterization data of the poly(vinyl benzoate) nanoparticles formed in this manner are described in Table 1. The size range of about 200-250 nm as analyzed by dynamic light scattering with a polydispersity index of around 0.2 indicate a highly homogeneous size distribution of nanoparticles. Scanning electron microscope (SEM) images (FIG. 3) showed spherical nanoparticles with a uniformly smooth surface and confirmed the mean diameter of about 200-250 nm. In contrast, poly(vinyl benzoate) nanoparticles prepared in the absence of Pluronic F68 were significantly larger in diameter, with a mean diameter of 490 nm. Thus, the surfactant not only stabilizes the nanostructures in aqueous media, but also significantly reduces the overall dimensions of the nanoparticles.

Particle size is an important physical property of nanoparticles directly affecting the cellular uptake capabilities, and ultimately, biodistribution. Cellular uptake is generally much greater for nanoparticles compared to microparticles (M. P. Desai, V. Labhasetwar, E. Walter, R. J. Levy, G. L. Amidon, The mechanism of uptake of biodegradable microparticles in Caco-2 cells is size dependent, Pharm. Res. 14 (11) (1997) 1568-1573). Hence, good cell penetration of the poly(vinyl benzoate) nanoparticles is expected due to their small size range, and Pluronic-F68 is known to facilitate cell penetration, as well as enhance in vivo stability and circulation lifetimes of the surfacted nanoparticles (E. Jeon, H. D. Kim, J. S. Kim, Pluronic-grafted poly-(L)-lysine as a new synthetic gene carrier, J. Biomed. Mater. Res. 66A (4) (2003) 854-859).

The zeta potential values for the coated nanoparticles were under −30 mV for each emulsion while −0.10 mV was obtained for the suspension without surfactant. The zeta potential is a very important factor to evaluate the stability of colloidal dispersion because particles are efficiently resuspended when the absolute value of the zeta potential is at least 30 mV due to the strong electric repulsion between particles (R. H. Müller, C. Jacobs, O. Kayser, Nanosuspensions as particulate drug formulations in therapy: rationale for development and what we can expect for the future, Adv. Drug Deliv. Rev. 47 (1) (2001) 3-19). Therefore, knowledge of the zeta potential can help to predict if the drug delivery system is suitable for intravenous administration due to the risk of nanoparticle agglomerations, which could result in microembolisms (P. Beck. J. Kreuter, R. Reszka, I. Fichtner, Influence of polybutylcyanoacrylate nanoparticles and liposomes on the efficacy and toxicity of the anticancer drug mitoxantrone in murine tumour models, J. Microencapsul. 10 (1) (1993) 101-114).

In Vitro Toxicity Experiments

Previous studies evaluated the potential cytotoxicity of nanoparticle emulsions and methods to remove unwanted, cidal impurities created during emulsion polymerization (J. Garay-Jimenez, A. Young, D. Gergeres, E. Turos, Methods for purifying and detoxifying sodium dodecyl sulfate-stabilized polyacrylate nanoparticles, Nanomed: Nanotech. Biol. Med. 4 (2) (2008) 98-105). Ideally, nanoparticles and all components of the media should induce no observable toxic effects on cells at or near the concentration levels needed for drug delivery. To ascertain this potential for poly(vinyl benzoate) nanoprecipitates, the samples were subjected to microbiological and mammalian toxicity assays. In vitro screening of the suspensions against representative bacteria (*S. aureus*, *E. coli*) indicate that the samples are not cidal to the microbes, nor do they inhibit bacterial growth on agar. Minimum inhibition concentration (MIC) values are above 256 µg/mL, which is above the upper limit of the testing.

TABLE 1

Characteristics of the PVBz nanoparticles

| Nanoparticle formulations | Particle Size (nm) | Polydispersity index | Zeta potential (mV) |
|---|---|---|---|
| Control with Pluronic P68 as surfactant | 256.6 ± 7.9 | 0.192 ± 0.016 | −29.2 ± 1.9 |
| Control without surfactant | 489.3 ± 6.7 | 0.381 ± 0.010 | −10.1 ± 0.4 |
| Coumarin-6-loaded nanoparticles | 222.8 ± 3.1 | 0.099 ± 0.042 | −56.6 ± 0.5 |
| 5(6)-Carboxyfluorescein-loaded nanoparticles | 206.2 ± 2.7 | 0.078 ± 0.007 | −43.6 ± 0.8 |

The results are expressed as the mean ± SD.

PACA nanoparticles have been found to have elevated cytotoxicity toward mammalian cell lines, in particular, human fibroblasts and epithelial tissue (C. Lherm, R. H. Miller, F. Puisieux, P. Couvreur, Alkylcyanoacrylate drug carriers: II. Cytotoxicity of cyanoacrylate nanoparticles with different alkyl chain length, Int. J. Pharm. 84 (1) (1992) 13-22; M. Brzoska, K. Langer, C. Coester, S. Loitsch, T. O. F. Wagner, C. V. Mallinckrodta, Incorporation of biodegradable nanoparticles into human airway epithelium cells—in vitro study of the suitability as a vehicle for drug or gene delivery in pulmonary diseases, Biochem. Biophys. Res. Commun. 318 (2) (2004) 562-570). Therefore, further in vitro testing was conducted on the poly(vinyl benzoate) nanoparticles using human epithelial cells (HaCaT) to assess possible toxicity, over a range of about 125 to 1000 μg/mL. IC50 values for the poly(vinyl benzoate) nanoparticles were greater than 1000 μg/mL, and even at this ultrahigh concentration, microscopic observation of the treated cells showed no discernible differences versus those of untreated cells.

In vitro cytotoxicity studies were also conducted against primary bovine aortic endothelial cells, over a range of nanoparticle concentrations ranging from 2 to 1000 μg/mL. IC50 values of the poly(vinyl benzoate) nanoparticles was above 500 μg/mL. Microscopic imaging of the treated cells showed no discernible differences after 48 hours versus those of untreated cells, at any of the concentrations. Poly(vinyl benzoate) nanoparticles are considered as non-cytotoxic in vitro given that 500 μg/mL represents a much higher intravenous material dose than required for in vivo drug delivery (J. M. Chan, L. Zhang, K. P. Yuet, G. Liao, J.-W. Rhee, R. Langer, O. C. Farokhzad, PLGA-lecithin-PEG core-shell nanoparticles for controlled drug delivery, Biomaterials 30 (8) (2009) 1627-1634).

Molecular Loading and Release Properties of the Nanoparticle

Two fluorescent markers have been used to evaluate the potential usefulness of the poly(vinyl benzoate) nanoparticles in drug delivery. Coumarin-6 and 5(6)-carboxyfluorescein were chosen to mimic hydrophobic and hydrophilic drugs respectively. Their lipophilicity has been previously established with the octanol/water partition coefficient (P) method which is expressed as the logarithm base 10 (log P). The reported log P for coumarin-6 is -3.45 (C. Lombry, C. Bosquillon, V. Préat, R. Vanbever, Confocal imaging of rat lungs following intratracheal delivery of dry powders or solutions of fluorescent probes, J. Control. Release (2002) 83 (3) 331-341) and 5.43 for 5(6)-carboxyfluorescein (K. Lahnstein, T. Schmehl, U. Rtlsch, M. Rieger, W. Seeger, T. Gessler, Pulmonary absorption of aerosolized fluorescent markers in the isolated rabbit lung, Int. J. Pharm. (2008) 351 (1-2) 158-164).

Figure 4:
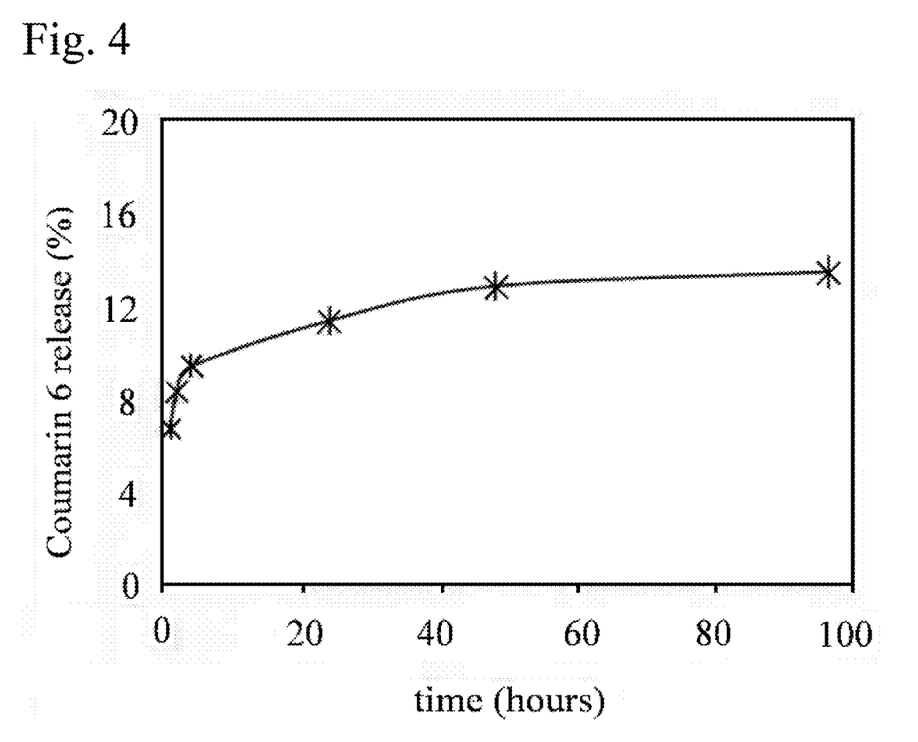
FIG. 4 is a graph showing the in vitro release profile of coumarin-6 from poly(vinyl benzoate) nanoparticles stabilized by Pluronic-F68. Incubation was maintained during 96 hours in PBS (pH 7.4, 10 mM) with 0.1% (w/v) Tween 80 at 37° C. Data represent average value of triplicates±S.D.

It was observed that nanoprecipitation of 100 mg of poly(vinyl benzoate) in the presence of Pluronic F68 and an initial amount of 2 mg of coumarin-6 occurred with a substantial encapsulation efficiency (78%) corresponding to a drug loading content of 1.56% of the dry polymer weight. Up to about 5% by weight of a drug may be encapsulated within the nanoparticle. FIG. 4 shows the in vitro release profile of coumarin-6 in PBS at 37° C. from fluorescently-labelled nanoparticles; a burst release of about 10% was observed in the first few hours followed by a much slower rate of release. Thus, even after 96 hours, less than 15% of the entrapped coumarin-6 is released from the nanoparticle.

In contrast. 5(6)-carboxyfluorescein allowed a poor loading efficiency (0.25%) leading to a total loading amount of 0.005% of the dry polymer weight (Table 2). The limit of detection by HPLC was further quantified, corresponding to about 5% of molecular release, and thus less than 5% of the entrapped 5(6)-carboxyfluorescein being liberated. The low amounts of burst release of the fluorophores from the nanoparticles indicates that the compounds are loaded by encapsulation rather than surface sorption. This supports the expectation that hydrophobic compounds would be confined inside the matrix of hydrophobic nanoparticles rather than associated loosely to the ionically-charged surface (J. Panyam, V. Labhasetwar, Biodegradable nanoparticles for drug and gene delivery to cells and tissue, Adv. Drug Deliv. Rev. 55 (3) (2003) 329-347; K. Y. Win, S.-S. Feng, Effects of particle size and surface coating on the cellular uptake of polymeric nanoparticles for oral delivery of anticancer drugs, Biomaterials 26 (15) (2005) 2713-2722).

TABLE 2

Influence of the marker lipophilicity on drug contents and encapsulation efficiency

| Marker loaded PVBz nanoparticles | Log P | Initial amount (mg) | Drug contents (% w/w) | Loading efficiency (% w/w) |
|---|---|---|---|---|
| Coumarin-6 | -3.45 | 2 | 1.56 ± 0.2 | 78 ± 3.1 |
| 5(6)-Carboxyfluorescein | 5.43 | 2 | 0.005 ± 0.0002 | 0.25 ± 0.08 |

The results are expressed as the mean ± S.D.

It was initially postulated that poly(vinyl benzoate) would likely biodegrade through a mechanism similar to that of PACA, i.e, enzymatic hydrolysis of the ester bond between the benzoate side chain and the polymeric backbone, with release of benzoic acid and poly(vinyl alcohol) (FIG. 1). However, there was no a priori information available indicating whether poly(vinyl benzoate) nanoparticles could undergo appreciable enzymatic degradation in media containing esterases, or be highly resistant to hydrolytic degradation. To investigate this, the inventors incubated the freshly-prepared poly(vinyl benzoate) nanoparticles in the presence of pig liver esterase at pH 7.4 in PBS as a model medium. The release of benzoic acid from the degradation of the poly(vinyl benzoate) nanoparticles was followed by HPLC. For this, three concentrations of nanoparticles (100, 500, and 1000 μg/mL) in PBS were incubated at 37° C. with pig liver esterase (100 U/mL). Every 24-hour, the supernatant was withdrawn and replaced with fresh medium containing 100 U/mL of pig liver esterase.

Figure 5:
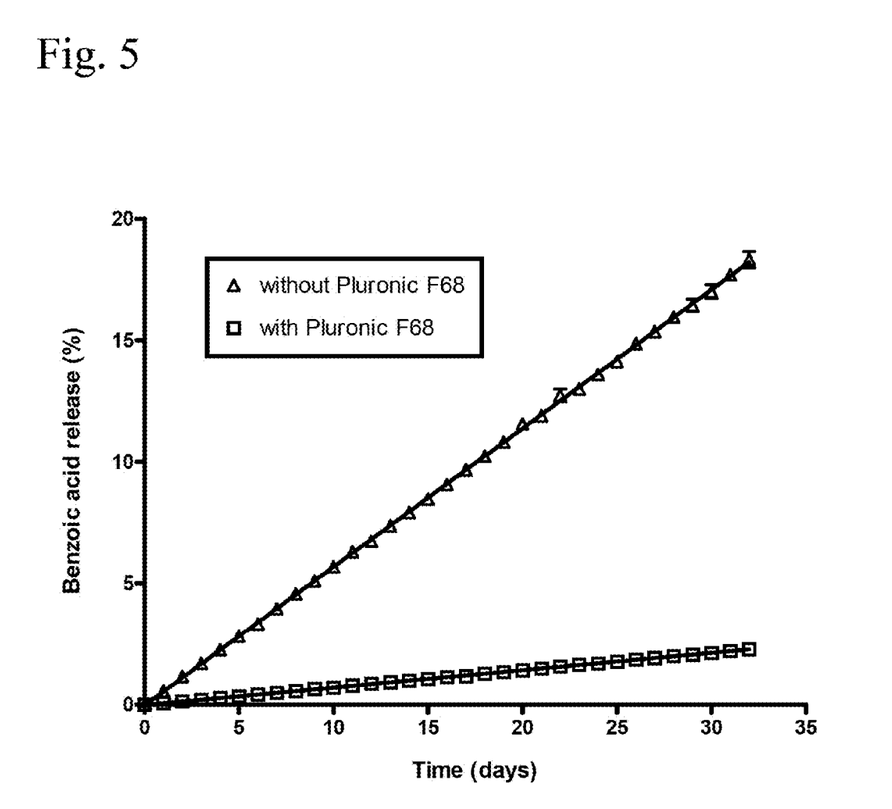
FIG. 5 is a graph showing the percentage of benzoic acid release from poly(vinyl benzoate) nanoparticles prepared with versus without Pluronic-F68. Incubation was maintained at 37° C. for 32 days in 10 mM PBS (pH 7.4) containing esterase (100 U/mL), with replacement of medium every 24 hours. Data represent average values of three experiments±S.D.

The inventors observed that the highest concentration of polymer produced the most significant amount of benzoic acid as detected by HPLC. To investigate the influence of Pluronic F68 on the enzymatic process, the same analysis was performed with poly(vinyl benzoate) nanoparticles prepared without surfactant. In this case, after incubation with esterases for 7 days, 4% of the benzoic acid was released as evidenced by HPLC analysis. After the same duration, assays with pluronic-coated nanoparticles liberated only 0.5% of benzoic acid. After 32 days, it was observed that 18% of the surfactant free-nanoparticles degraded while only 2% of the benzoic acid was detected for the nanoparticles with Pluronic F68 (FIG. 5). These data suggest that it would take about 5 months for the full release of benzoic acid in the case of nanoparticles without surfactant and about 4 years for the pluronic-coated nanoparticles, when esterase is present in the media.

Figure 6:
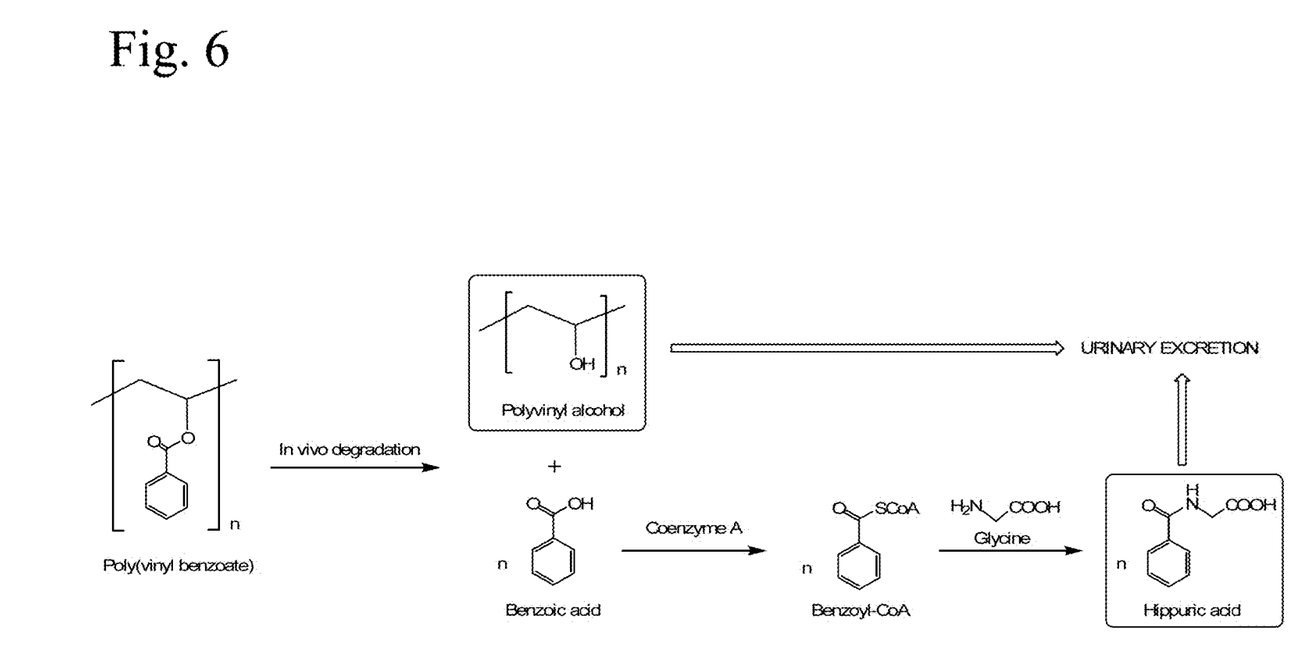
FIG. 6 is a chemical diagram showing the postulated in vivo metabolism of poly(vinyl benzoate).

The relative difference in enzymatic degradation rates observed between the stabilized versus unstabilized nanoparticles shows the propensity for pluronics to resist enzymatic degradation. Indeed, previous studies have shown that the surface properties of polymeric nanomaterials greatly influence the rate of degradation and systemic lifetimes (Z. Gan, D. Yu, Z. Zhong, Q. Liang, X. Jing, Enzymatic degradation of poly(s-caprolactone)/poly(DL-lactide) blends in phosphate buffer solution, Polymer 40 (10) (1999) 2859-2862). Furthermore, the slow degradation of the poly (vinyl benzoate) nanoparticles by esterases indicates the difficulty for enzymatic process to take place on a hydrophobic polymer nanoparticle. Other chemical and enzymatic components in a complex living system may increase metabolic rates, as has been observed for poly($\epsilon$-caprolactone) (J. S. Chawla, M. M. Amiji, Biodegradable poly ( caprolactone) nanoparticles for tumor-targeted delivery of tamoxifen, Int. J. Pharm. 249 (1) (2002) 127-138). Nevertheless, with the observation that the poly(vinyl benzoate) nanoparticles undergo (albeit sluggish) side chain scission of the benzoate ester linkage, a metabolic pathway is proposed for the nanoparticle degradation (FIG. 6). The molecular weight of the hydrolysis by-product, poly(vinyl alcohol), should be below the renal threshold barrier and subsequently eliminated from the body primarily by renal excretion without metabolic modification (A. Besheer, K. Mider, S. Kaiser, J. Kressler, C. Weis, E. K. Odermatt, Tracking the urinary excretion of high molar mass poly(vinyl alcohol), J. Biomed. Mater. Res. 82B (2) (2007) 383-389; T. Yamaoka, Y. Tabat, Y. Ikada, Comparison of body distribution of poly(vinyl alcohol) with other water-soluble polymers after intravenous administration, J. Pharm. Pharmacol. 47 (6) (1995) 479-486). The second byproduct, benzoic acid, undergoes metabolic conversion to a benzoyl coenzyme A (CoA) adduct, which is transamidated with glycine to produce hippuric acid, a compound that is exported from the liver to the kidney to be excreted in the urine (L. Krähenbühl, J. Reichen, C. Talos, S. KrihenbUhl, Benzoic acid metabolism reflects mitochondrial function in rats with long-term extrahepatic cholestasis, Hepatology 25 (2) (1997) 278-283).

Stability in Blood Serum

Figure 7:
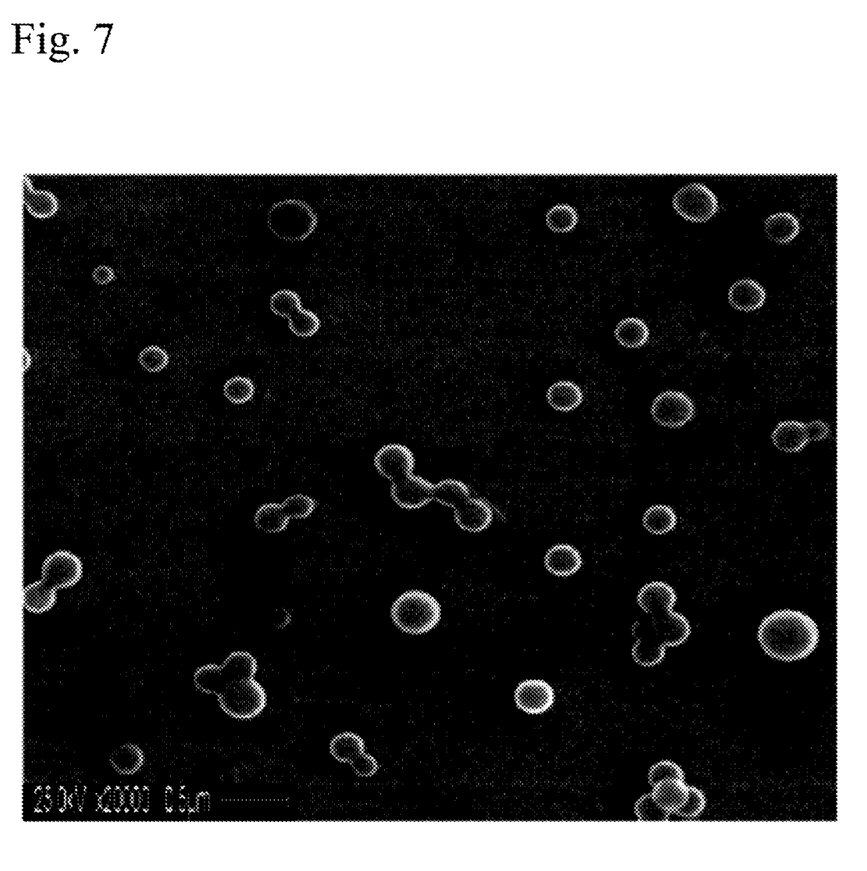
FIG. 7 is a SEM micrograph of poly(vinyl benzoate) nanoparticles after 8 days in rat serum at 37° C.

The stability of poly(vinyl benzoate) nanoparticles in serum was evaluated to further predict their potential for intravenous administration. Freeze-dried nanoparticles were resuspended in deionized water then mixed with rat serum and incubated at 37° C. The nanoparticles are stable in serum even after 8 days, keeping their original shape and size as seen in the SEM micrograph (FIG. 7). Retaining their smooth morphological features and non-agglomerated state should reduce the risk of microembolism and organ infraction caused by large coagulates in the blood (P. Beck, J. Kreuter, R. Reszka, I. Fichtner, Influence of polybutylcyanoacrylate nanoparticles and liposomes on the efficacy and toxicity of the anticancer drug mitoxantrone in murine tumour models, J. Microencapsul. 10 (1) (1993) 101-114).

CONCLUSION

Nanoprecipitation of commercial poly(vinyl benzoate) in the presence of Pluronic F68 produces nanoparticles with smooth surfaces and with a mean diameter of about 200-250 nm. The nanoparticles are non-toxic towards human and bacterial cell lines. A hydrophobic model drug compound, coumarin-6, was efficiently encapsulated (up to 1.56% by weight) while the hydrophilic fluorophore, 5(6)-carboxyfluorescein, gave low compound entrapment. Up to 5% by weight of a hydrophobic or lipophilic drug may be encapsulated within the nanoparticle. Nanoparticles exhibited slow, controlled release in PBS. Degradation of the nanoparticles in the presence of esterases proceeded via side chain hydrolysis to release benzoic acid as an indicator of bioerosion. Pluronic F68 was found to retard hydrolytic degradation, with about 5% of benzoic acid release occurring within the first 32 days, while nanoparticles without surfactant were degraded approximately ten times faster. Furthermore, the poly(vinyl benzoate) nanoparticles, when protected by Pluronic F68, are stable in rat serum.

The disclosures of all publications cited above are expressly incorporated herein by reference, each in its entirety, to the same extent as if each were incorporated by reference individually.

It is also to be understood that the following claims are intended to cover all of the generic and specific features of the invention herein described, and all statements of the scope of the invention which, as a matter of language, might be said to fall there between. Now that the invention has been described,

What is claimed is:

1. A composition of nanoparticles comprising:
   at least one biodegradable nanoparticle formed from poly(vinyl benzoate) and a block copolymer based on ethylene oxide and propylene oxide wherein the at least one nanoparticle is capable of entrapping lipophilic substrates;
   a pharmaceutically acceptable carrier; and
   a lipophilic molecules.

2. The composition of claim 1, wherein the surfactant prevents opsonization.

3. The composition of claim 1, wherein the at least one nanoparticle has a mean particle size of between about 50 nm and about 350 nm.

4. The composition of claim 1, wherein the at least one nanoparticle has a mean particle size of between about 200 nm and about 250 nm.

5. The composition of claim 1, wherein the size of the lipophilic molecule is up to about 5% by weight.

6. The composition of claim 1, wherein the lipophilic molecule is an antibacterial agent.

7. The composition of claim 1, wherein the lipophilic molecule is a drug.

8. A method of generating a small molecular drug carrier comprising:
   nanoprecipitation of a polymer, further comprising
      adding at least one surfactant to water, where the at least one surfactant is a block copolymer based on ethylene oxide and propylene oxide;
   dissolving or diluting poly(vinyl benzoate) in acetone;
   dissolving a predetermined quantity of lipid-soluble molecule in the acetone;
   adding the poly(vinyl benzoate)-acetone solution to the water to form a mixture of a block copolymer based on ethylene oxide and propylene oxide and poly(vinyl benzoate);
   stirring the mixture of a block copolymer based on ethylene oxide and propylene oxide and poly(vinyl benzoate); and
   evaporating the acetone from the mixture of a block copolymer based on ethylene oxide and propylene oxide and poly(vinyl benzoate) to leave a suspension of polyvinyl benzoate nanoparticles.

9. The method of claim 8, wherein the poly(vinyl benzoate) is added at about 0.5% (w/v) to the acetone.

10. The method of claim 8, wherein the a block copolymer based on ethylene oxide and propylene oxide is added at about 0.5% w/v.

11. The method of claim 8, wherein the acetone is evaporated overnight at room temperature.

12. The method of claim 8, further comprising washing the polyvinyl benzoate nanoparticles, further comprising:
  centrifuging the suspension of polyvinyl benzoate nanoparticles at 10,000 rpm for 10 minutes;
  resuspending the pellet formed from the centrifugation in distilled water; and
  sonicating the pellet for 1 minute to disperse any aggregates.

13. The method of claim 8, further comprising:
  freezing the polyvinyl benzoate nanoparticles at −70° C.; and
  lyophilizing the polyvinyl benzoate nanoparticles for 24 hours.

\* \* \* \* \*

UNITED STATES PATENT AND TRADEMARK OFFICE
CERTIFICATE OF CORRECTION

| | | |
|---|---|---|
| PATENT NO. | : 9,433,581 B2 | Page 1 of 1 |
| APPLICATION NO. | : 13/897868 | |
| DATED | : September 6, 2016 | |
| INVENTOR(S) | : Edward Turos et al. | |

It is certified that error appears in the above-identified patent and that said Letters Patent is hereby corrected as shown below:

In the Claims

Column 18, Claim 1, Line 26 should read:

a lipophilic molecule.

Signed and Sealed this
Fifteenth Day of November, 2016

Michelle K. Lee
*Director of the United States Patent and Trademark Office*